US008465700B2

(12) United States Patent
Huang

(10) Patent No.: US 8,465,700 B2
(45) Date of Patent: Jun. 18, 2013

(54) HIGH-THROUGHPUT SOLVENT EVAPORATOR AND GAS MANIFOLD WITH UNIFORM FLOW RATES AND INDEPENDENT FLOW CONTROLS

(75) Inventor: Yongsong Huang, Barrington, RI (US)

(73) Assignee: Brown University, Providence, RI (US)

( * ) Notice: Subject to any disclaimer, the term of this patent is extended or adjusted under 35 U.S.C. 154(b) by 761 days.

(21) Appl. No.: 12/303,226

(22) PCT Filed: May 31, 2007

(86) PCT No.: PCT/US2007/070040

§ 371 (c)(1), (2), (4) Date: Dec. 2, 2008

(87) PCT Pub. No.: WO2007/143484

PCT Pub. Date: Dec. 13, 2007

(65) Prior Publication Data

US 2009/0191099 A1 Jul. 30, 2009

Related U.S. Application Data

(60) Provisional application No. 60/810,392, filed on Jun. 2, 2006.

(51) Int. Cl.
*G01N 33/00* (2006.01)

(52) U.S. Cl.
USPC ................................ 422/83; 422/93; 422/500

(58) Field of Classification Search
USPC ................................ 422/83, 93, 500
See application file for complete search history.

(56) References Cited

U.S. PATENT DOCUMENTS

| | | | | |
|---|---|---|---|---|
| 4,810,471 | A * | 3/1989 | Wachob et al. | 422/540 |
| 2003/0215957 | A1 | 11/2003 | Lemmo et al. | |

* cited by examiner

*Primary Examiner* — Sam P Siefke
(74) *Attorney, Agent, or Firm* — Barlow, Josephs & Holmes, Ltd.

(57) ABSTRACT

The evaporator (10) efficiently evaporates solvent and/or introduces gases to multiple samples. The evaporator (10) contains a top plate (20) and a bottom plate (30). The top plate (20) is mated to the bottom plate (30) to define a main chamber (130) for distribution of gas. An input port (80) is defined within the bottom plate (30) of the evaporator (10) is in fluid communication with a gas distribution channel (100). The gas distribution channel (100) has a series of gas distribution ports (110A-C) increasing in diameter, in proportion to a distance from the input port (80), that provide for an even distribution of gas into the main chamber (130). Gas exits the main chamber (130) through exit ports (120A-C) defined within the bottom plate (30). Screws (50) respectively control gas flow to exit ports (120A-C) for delivery to an array of nozzles (90) on the bottom plate (30).

15 Claims, 7 Drawing Sheets

HIGH-THROUGHPUT SOLVENT EVAPORATOR AND GAS MANIFOLD WITH UNIFORM FLOW RATES AND INDEPENDENT FLOW CONTROLS

CROSS REFERENCE TO RELATED APPLICATION

This application is related to and claims priority from earlier filed U.S. provisional patent application Ser. No. 60/810,392, filed Jun. 2, 2006 and incorporated herein by reference.

BACKGROUND OF THE INVENTION

It is often necessary to evaporate solvents from a solution or suspension as a step in processing or concentrating a sample of material for instrumental analysis. For example, in the geological and environmental sciences, one needs to evaporate solvent from samples of solvent extracts of sediment and soil samples, as well as various fractions of compounds resulting from chromatographic isolation steps.

Gas often needs to be introduced to multiple reaction vessels during parallel reactions or synthesis such as hydrogenation of unsaturated organic compounds. The standard method for accomplishing these is to pass a gas that is under pressure over the surface of the sample or into the solution. The configuration of the sample holder, the temperature of the sample and/or of the pressurized gas, the composition of the gas and the need to work in an environment where human exposure to the sample and gas is controlled are features which are well recognized as affecting the desired evaporation.

Individual samples are easily processed. For example, a sample of soil extracts suspended in ethanol and contained in a test tube might be dried by evaporation of the ethanol solvent by passing a stream of pressurized nitrogen gas through a pipette over the sample.

However, often one needs to process a number of samples for analysis. Devices which can be used to facilitate multiple samples processing including those that hold multiple samples and those which use evaporators capable of delivering several streams of pressurized gas simultaneously are known. For example, see the 6-Port Mini-Vap, item 201006 in the online catalog at www.chromes.com or the MiniVap Sample Concentrator in the online catalog of Artic White (www.articwhiteusa.com).

Shortcomings of known devices, such as those above, include the fact that the flow of gas from all nozzles in an evaporator is not equal and individual nozzles can not be controlled individually (that is, all are on or all are off). This leads to disparity in the rate of evaporation of solvent such that at any given time, some samples are dried faster than others and this can lead to undesired variations in subsequent processing steps or analyses. Also, the "all-on or all-off" configuration can lead to waste of the pressurized gas if not all nozzles in a evaporator are being used, and also cause dust/contaminants being blown up from unused ports that can contaminate samples in ports being used. When concentrating solutes with relatively high volatility, excessive blowing with nitrogen when solvent is already removed can lead to sample losses and subsequent error in analytical results.

In view of the foregoing, there is a need for a high-throughput evaporator to provide an even gas distribution for multiple samples. In addition, there is a need for an evaporator that has adjustable and independent flow control over gas exiting the evaporator for each sample. Also, there is a need for an evaporator that minimizes the leakage of gas.

SUMMARY OF THE INVENTION

An embodiment of the present invention preserves the advantages of prior evaporators. In addition, it provides new advantages not found in currently available evaporators and overcomes many disadvantages of such currently available evaporators.

The present invention is an evaporator that can be used to efficiently evaporate solvent from sample materials and/or to introduce gases to multiple reaction media. The evaporator contains a top plate having an inner and outer surface and a bottom plate having an inner and outer surface. The inner surface of the top plate is mated to the inner surface of the bottom plate to define a main chamber for distribution of gas. In one embodiment, a gasket is dispersed between the top plate and the bottom plate to provide a non-permeable seal.

An input port for delivery of gas into the evaporator is defined within the bottom plate. The input port penetrates through a side wall of the bottom plate for fluid communication with a gas distribution channel defined within the bottom plate. The gas distribution channel having a series of gas distribution ports increasing in diameter, in proportion to a distance from the input port, provides for an even distribution of gas into the main chamber. In one embodiment, the gas distribution channel has three ports of increasing diameter.

The outer surface of the bottom plate has an array of nozzles used for delivery of gas from the evaporator and into contact with respective samples. In one embodiment, the nozzle is a needle attached to the outer surface of the bottom plate using a Leur lock. In a preferred embodiment, the outer surface of the bottom plate contains twenty-four needles arranged in a 4×6 array.

The inner surface of the bottom plate defines a series of exit ports for the exit of gas from the main chamber. In one embodiment, the inner surface of the bottom plate defines twenty-four exit ports arranged in a 4×6 array. Furthermore, the exit ports extend through the bottom plate for fluid communication with the nozzles.

The top plate has an array of female threaded bores for respectively threading receiving screws therein. The screws are independently adjustable to control gas through the nozzles. The screws extend through the top plate for receipt within and proximal to the exit ports. In a preferred embodiment, the twenty-four nylon screws are arranged in a 4×6 array.

The screws have tips that are shaped to closely conform to the top ends of the exit ports in the bottom plate. The screws can be independently positioned in varied positions to achieve the desired gas flow rate out of the nozzles via the exit ports. When in a closed position, the screws preclude the gas flow out of the nozzle.

In use, a gas is introduced into the evaporator through the input port and flows into the gas distribution channel. Next, the gas travels through the gas distribution ports of the gas distribution channel to provide an even distribution of gas into the main chamber. The gas exits the main chamber through the exit ports at a gas flow rate depending on the respective adjustment of the screws. Subsequently, the gas exits the exit ports and through nozzles for delivery of the gas into contact with a sample.

It is therefore an object of the evaporator to provide an even gas distribution for each nozzle.

It is a further object of the embodiment to provide an evaporator with independent and adjustable gas flow through each nozzle.

Another object of the embodiment to provide an evaporator that reduces leakage of pressurized gas.

BRIEF DESCRIPTION OF THE DRAWINGS

The novel features which are characteristic of the evaporators are set forth in the appended claims. However, the evaporator, together with further embodiments and attendant advantages, will be best understood by reference to the following detailed description taken in connection with the accompanying drawings in which:

DETAILED DESCRIPTION OF THE PREFERRED EMBODIMENT

Figure 1:
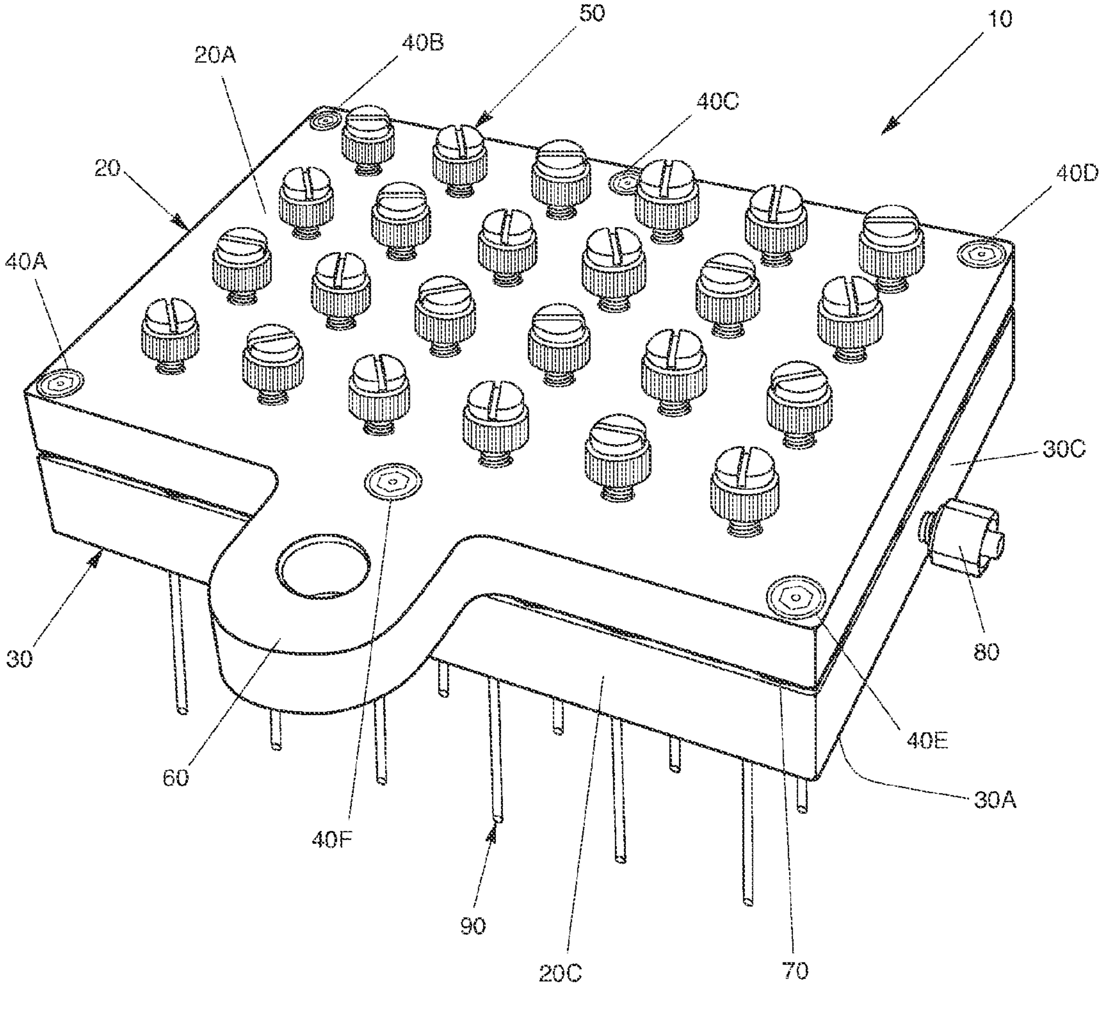
FIG. 1 is a top perspective view of the evaporator of the present invention.

Referring to FIG. 1, a top perspective view of an evaporator 10 is shown in accordance with the present invention. The evaporator 10 allows for high-throughput solvent evaporation by equalizing distribution of gas. In addition, the evaporator 10 allows for independent and adjustable gas flow based upon the requirements of the experiment. Also, the evaporator 10 is designed to minimize leakage of pressurized gas.

The evaporator 10 is constructed of materials resistant to organic solvents that can be machined easily. In a preferred embodiment, the material used within the evaporator 10 is aluminum. However, other compositions, such as other metals (i.e. nickel plated aluminum) or plastics (i.e. Teflon, polypropylene, nylon) are also possible for use in the evaporator 10.

Still referring to FIG. 1, the evaporator 10 consists of a top plate 20 and a bottom plate 30. The top plate 20 and the bottom plate 30 are joined together to form a block shape that provides minimal leakage of pressurized gas. To further minimize the leakage of pressurized gas, a gasket 70 is positioned between the top plate 20 and the bottom plate 30 when joined together. To provide a sufficiently tight fit, the top plate 20 and the bottom plate 30 are fastened together, for example, using six bolts 40A-F. Other means to join the top plate 20 and the bottom plate 30 together may be used to provide a seal sufficient to minimize the leakage of pressurized gas.

An outer surface 20A of the top plate 20 includes an independent and adjustable mechanism for controlling gas flow. For example, the independent and adjustable mechanism is preferably an array of screws 50. Each screw 50, in one embodiment, is made of plastic (i.e. nylon) or other durable materials that are non-permeable. In a preferred embodiment, the top plate 20 employs twenty four nylon screws 50 in a 4×6 array. For more precise controls and minimization of gas leakage, individual needle valves (not shown) can also replace the screws 50.

The evaporator 10 may also be part of another concentrator or evaporator device (not shown). To facilitate the attachment of the evaporator 10 to another concentrator or evaporator device, a front wall 20C of the top plate 20 has an integrally formed flange 60 with a hole in the center. The flange 60 may be used for attachment to another sample concentrator or evaporating device. In function, the evaporator 10 may be used as a gas manifold when attached to another concentrator/evaporator device.

The bottom plate 30 also contains an input port 80 positioned within a side wall 30C of the bottom plate 30. The input port 80 provides pressurized gas into the evaporator 10 with minimal leakage. Also, the input port 80 has a length sufficient to penetrate through the side wall 30C of the bottom plate 30. The input port 80 may be threadably and releasably connected to bottom plate 30 to permit easy replacement or permanently connected thereto. In addition, the bottom plate 30 has a series of nozzles 90 attached to an outer surface 30A of the bottom plate 30, which is discussed further below.

Figure 2:
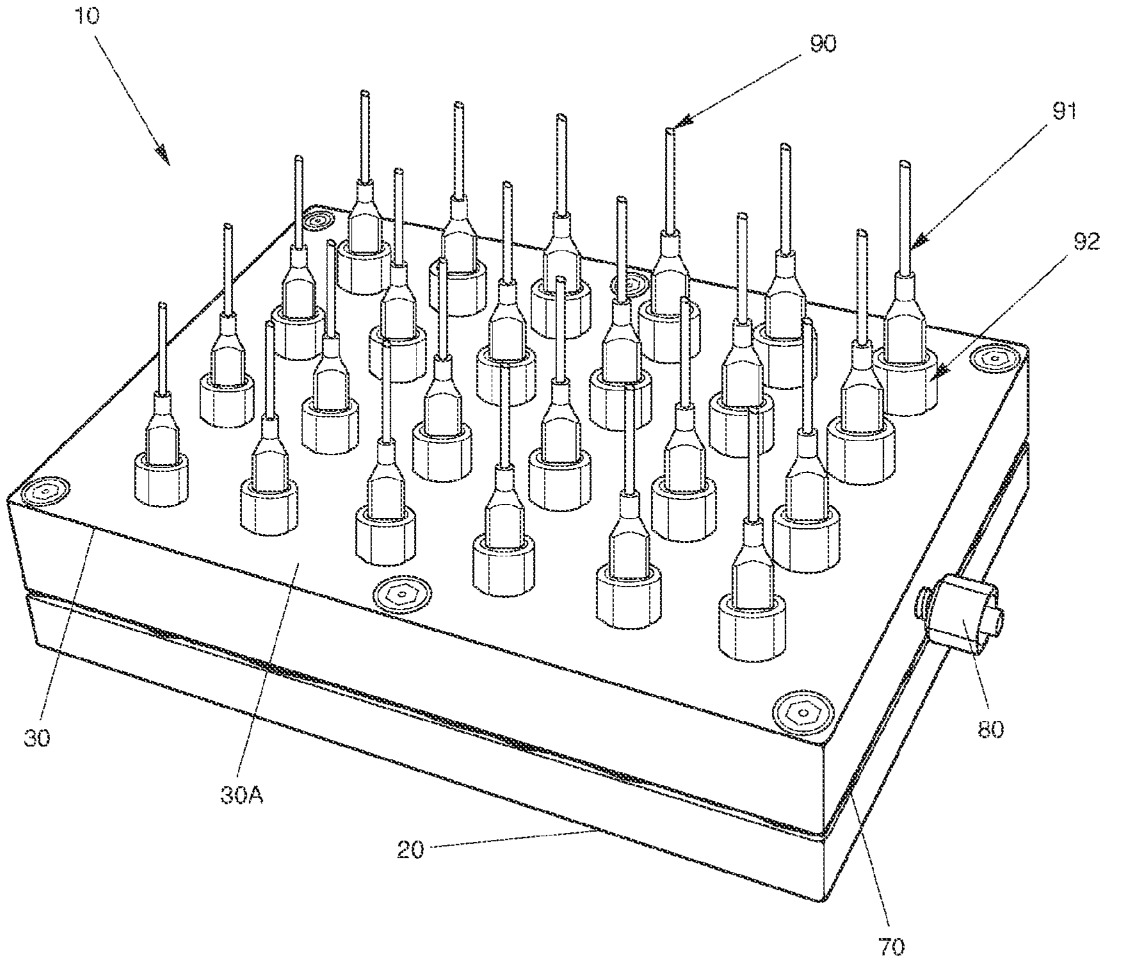
FIG. 2 is a bottom perspective view of the evaporator of FIG. 1.

Referring now to FIG. 2, a bottom perspective view of the evaporator 10 is shown. The outer surface 30A of the bottom plate 30 has an array of nozzles 90 used for delivery of gas from the evaporator 10 and into contact with an array of samples. It should be appreciated that a device other than a nozzle 90 may be used to deliver gas into contact with a sample.

In one embodiment, the nozzle 90 is a stainless steel needle 91 that is approximately 5" long and connected to the outer surface 30A of the bottom plate 30 using a Leur lock 92. This allows for easy exchange of the needle 91 for cleaning or replacement. However the composition of the nozzle 90 including the degree of flexibility and the shape of the orifice can be modified. In a preferred embodiment, the outer surface 30A of the bottom plate 30 contains twenty-four needles 91 having a uniform length and arranged in a 4×6 array. Any array may be employed and still be within the scope of the present invention.

Figure 3A:
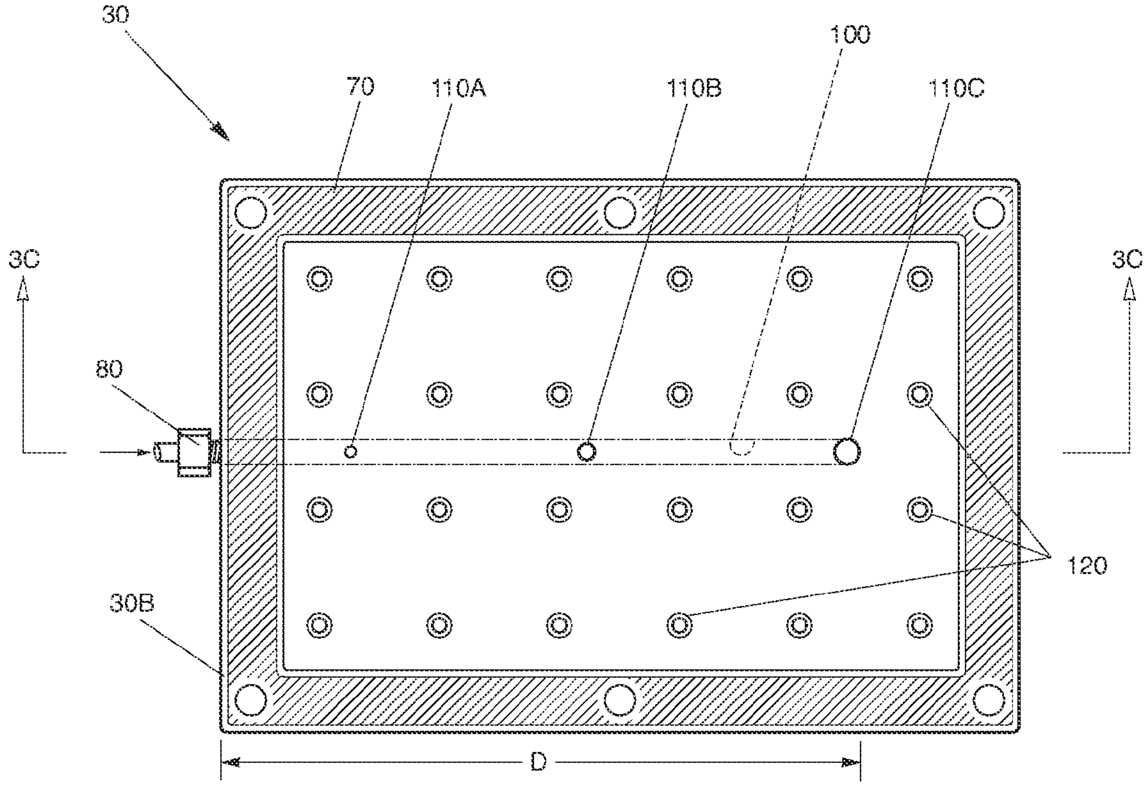
FIG. 3A is a top view of the bottom plate of the evaporator of FIG. 1.

Referring to FIG. 3A, the gasket 70 is positioned on the outer periphery edge of an inner surface 30B of the bottom plate 30. Also, the gasket 70 has pre-cut holes for receipt of the bolts 40A-F used to fasten the top plate 20 to the bottom plate 30. The gasket 70 is made of durable, non-permeable materials suitable to prevent leakage of gas.

Still referring to FIG. 3A, the input port 80 is in fluid communication with a gas distribution channel 100 defined within the bottom plate 30. The gas distribution channel 100 extends horizontally from the side wall 30C of the bottom plate 30 and along a substantial length of the bottom plate 30. The gas distribution channel 100 has a series of gas distribution ports 110A-C defined therein. At least one gas distribution port is defined within the gas distribution channel 100. In a preferred embodiment, the number of gas distribution ports 110A-C contained within the gas distribution channel 100 is three.

The diameter of the gas distribution ports 110A-C increases in proportion to a distance (D) from the input port 80. In other words, the greater the distance (D) of the gas distribution ports 110A-C from the input port 80, then the greater the diameter of the gas distribution ports 110A-C. For example, the first gas distribution port 110A (closest to the input port 80) has a smaller diameter than the second gas distribution port 110B, which has a smaller diameter than the third gas distribution port 110C. The proportionate diameter of the gas distribution ports 110A-C, in relation to its distance from the input port 80, facilitates the even distribution of gas. The sizes of these gas distribution ports 110A-C may be modified to start the application at hand. For example, the first input port may be 1/16", the second input port may be 3/32", and the third input port may be 1/8".

In FIG. 3A, the inner surface 30B of the bottom plate 30 defines a series of exit ports 120 for the exit of gas. In one embodiment, the inner surface 30B of the bottom plate defines twenty-four exit ports 120 arranged in a 4×6 array. However, it should be noted that a number of exit ports 120 other than twenty-four can be arranged in different arrays.

Figure 3B:
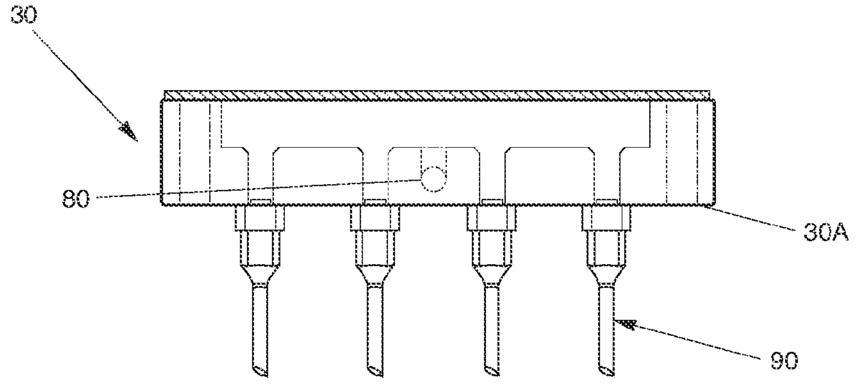
FIG. 3B is a right side view of the bottom plate of the evaporator of FIG. 1 showing gas flow within the interior of the bottom plate.

Furthermore, as shown in FIG. 3B, the exit ports 120 extend through the bottom plate 30 for engagement with the nozzles 90. It is preferred that the exit ports 120 are equally distanced from one another and have a uniform diameter. Alternatively, the exit ports 120 are non-equally distanced and have a non-uniform diameter.

The nozzles 90 attached to the bottom plate 30 fluidly communicate with exit ports 120. The nozzles 90 are respectively positioned beneath the exit ports 120 for delivery of gas into contact with a sample. The nozzle 90, in a preferred embodiment, is immediately adjacent to the outer surface 30A of the bottom plate 30 for receipt of the gas exiting ports 120. By placing the nozzle 90 immediately adjacent to the outer surface 30A, it reduces the leakage of pressurized gas.

Figure 3C:
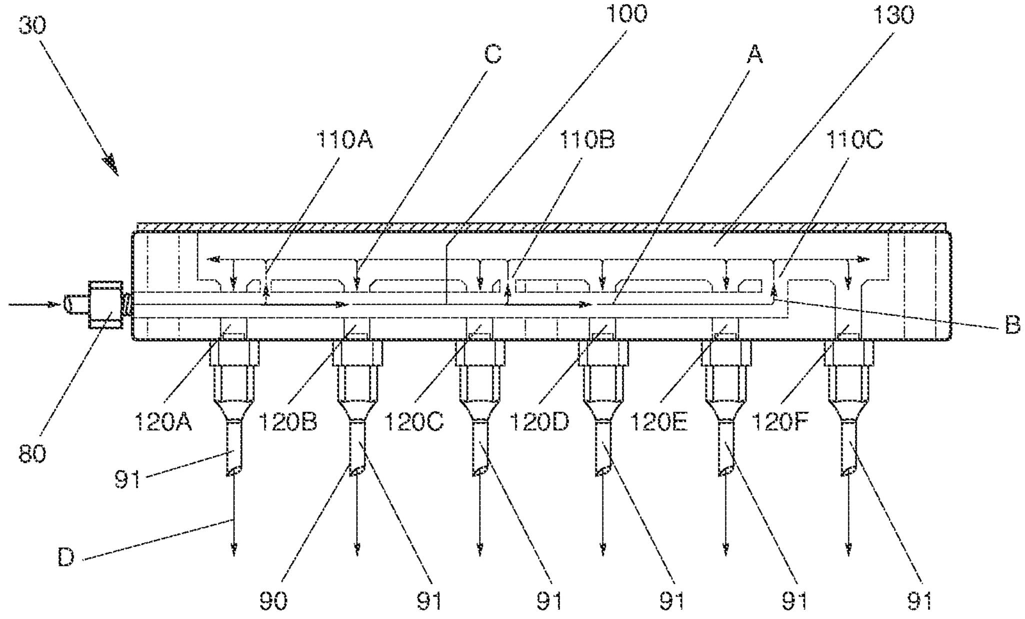
FIG. 3C is a front side view of the bottom plate of the evaporator of FIG. 1.

Referring to FIG. 3C, a diagram of the gas flow within the bottom plate 30 is shown. First, pressurized gas (i.e. nitrogen, argon) is introduced into the input port 80. The gas travels through the input port 80 and up into the gas distribution channel 100. The gas distribution channel 100 defines gas distribution ports 110A-C with increasing diameter. It should be noted there can be more gas distribution ports if a mix of gases is used. Of course, less than three gas distribution ports may be utilized.

Still referring to FIG. 3C, the gas distribution ports 110A-C defined within the gas distribution channel 100 equalizes the distribution of gas. The gas distribution ports 110A-C provide gas in proportion to the size of the gas distribution port 110A-C and its distance from the input port 80. For example, the first gas distribution port 110A is closer to the input port 80 than the second gas distribution port 110B. However, the first gas distribution port 110A is smaller in diameter than the second gas distribution port 110B. As a result, the volume of gas moving through the first port 110A and second port 110B is equalized. This equalization of gas would also apply to the third port 110C in relation to the first port 110A and the second port 110B as well.

As shown in FIG. 3C, the inflow gas shown in line A (gas entering from the input port 80) and the outflow gas shown in line D (gas exiting the nozzles 90) moves in opposite directions. This eliminates the possibility that nozzles 90 situated closer to the gas distribution ports 110A-C of the gas distribution channel 100 may have higher outflow gas rates. The design also allows for equal outflow rates in the nozzles 90.

Figure 4A:
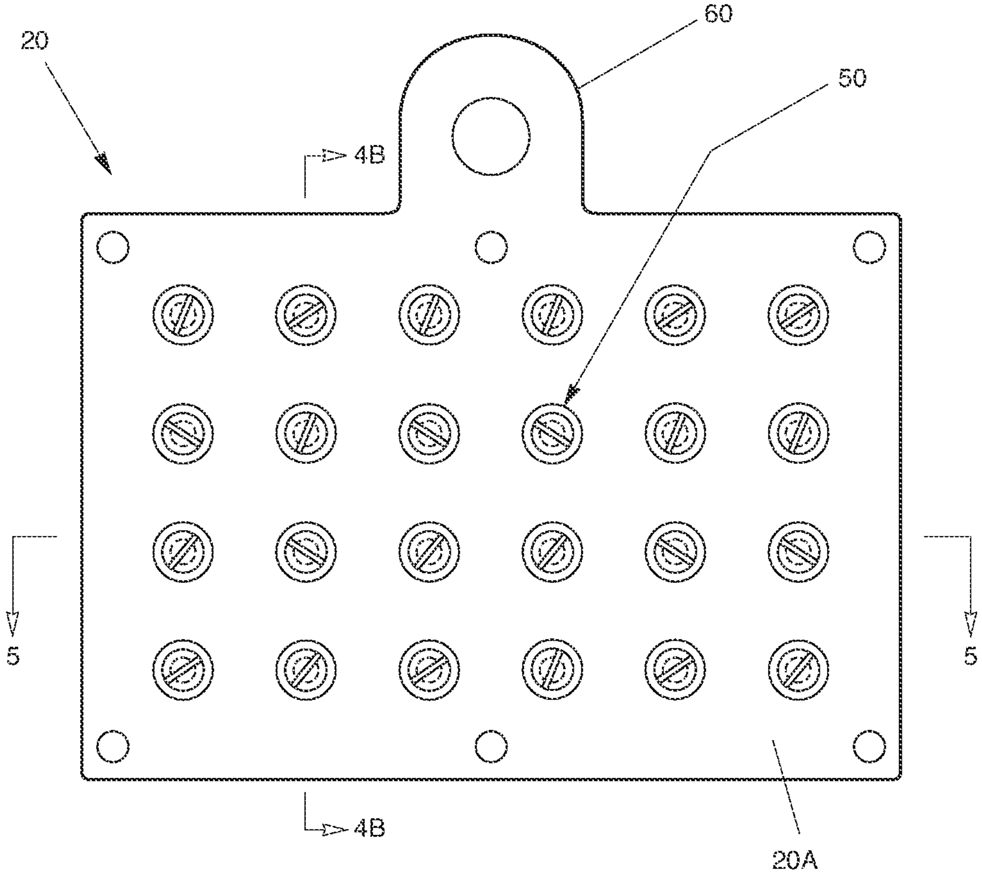
FIG. 4A is a top view of the top plate of the evaporator of FIG. 1.

Referring to FIG. 4A, the top plate 20 has screws 50 in varied positions. The screws 50 may be independently adjusted and positioned in different positions to respectively control gas flow through the nozzles 90. It should be appreciated that other devices, such as needles (not shown), may be used alternatively. An added benefit of using the screws 50 is that they threadably engage embed within the top plate 20 to prevent misplacement of the screws 50.

Figure 4B:
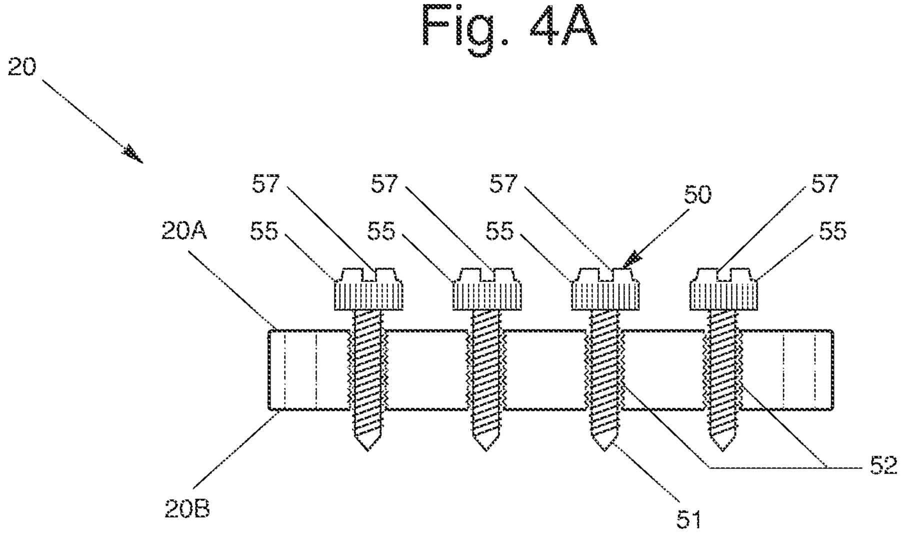
FIG. 4B is a left side partial cross-sectional view of the top plate of the evaporator through the line 4B-4B of FIG. 4A.

Referring to FIG. 4B, a left side partial cross-sectional view of the top plate 20 is shown. The screws 50 are threadably received within female threaded bores 52 of the top plate 20. The screw 50 extends from the outer surface 20A of the top plate 20 to an inner surface 20B of the top plate 20. The screw 50 penetrates through the top plate 20. The screws 50 have a male thread 53 for thread adjustable movement within the top plate 20 and for adjusting the length of the screw 50 protruding from the inner surface 20B of the top plate 20. Slots 57 in the heads 55 of the screws 50 facilitate adjustment with the use of a flat-head screw driver. Heads 55 may also be knurled for manual hand adjustment without tools.

Figure 5:
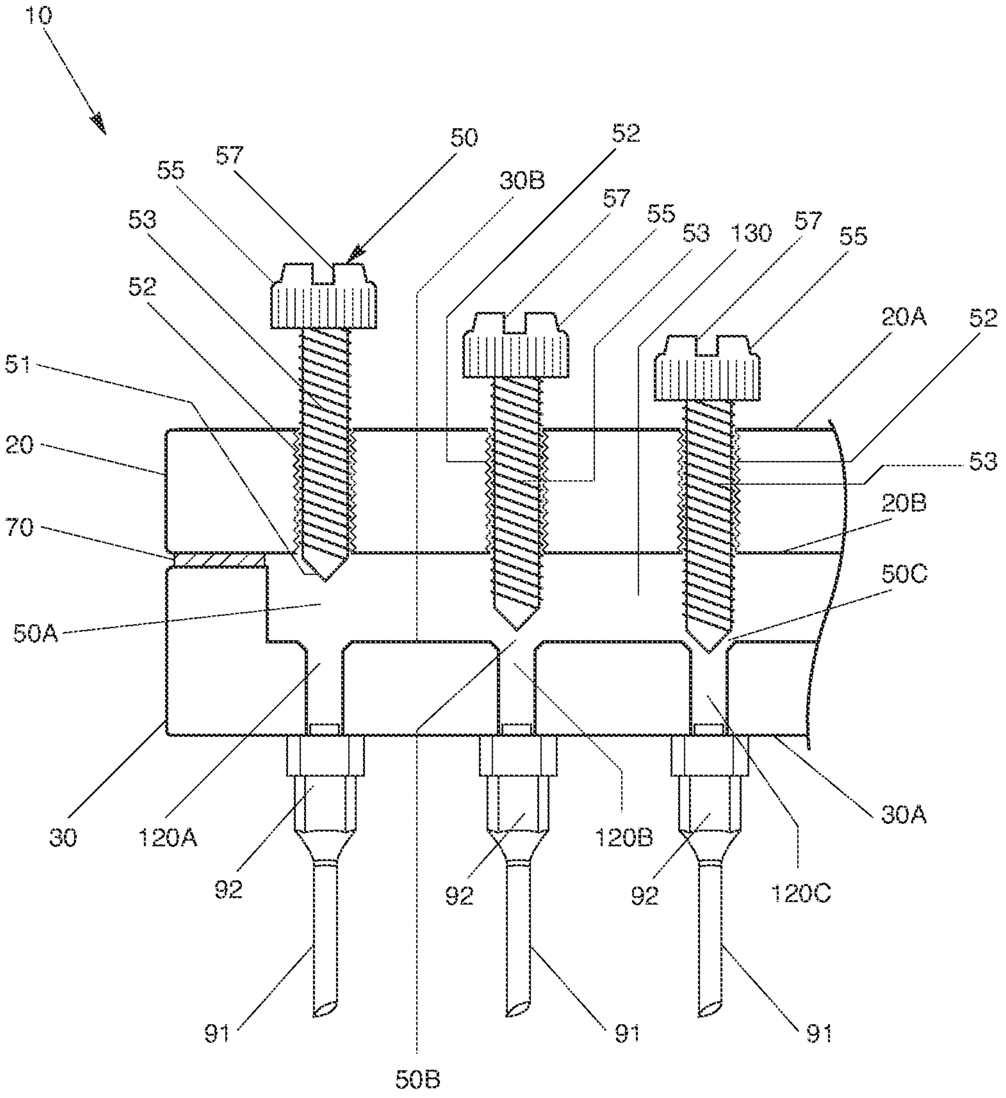
FIG. 5 is a cross-sectional view through the line 5-5 of FIG. 4A of the evaporator with multiple screw positions.

Referring to FIG. 5, a cross-sectional view of the evaporator 10 with multiple screw positions is shown. The top plate 20 and the bottom plate 30 are joined together to define a main chamber 130 used for even distribution of gas. In a preferred embodiment, the main chamber 130 is 3/8" in height, but a wide spectrum of sizes for the main chamber 130 could be used. The main chamber 130 receives gas and distributes gas evenly to the exit ports 120A-C.

Figure 6:
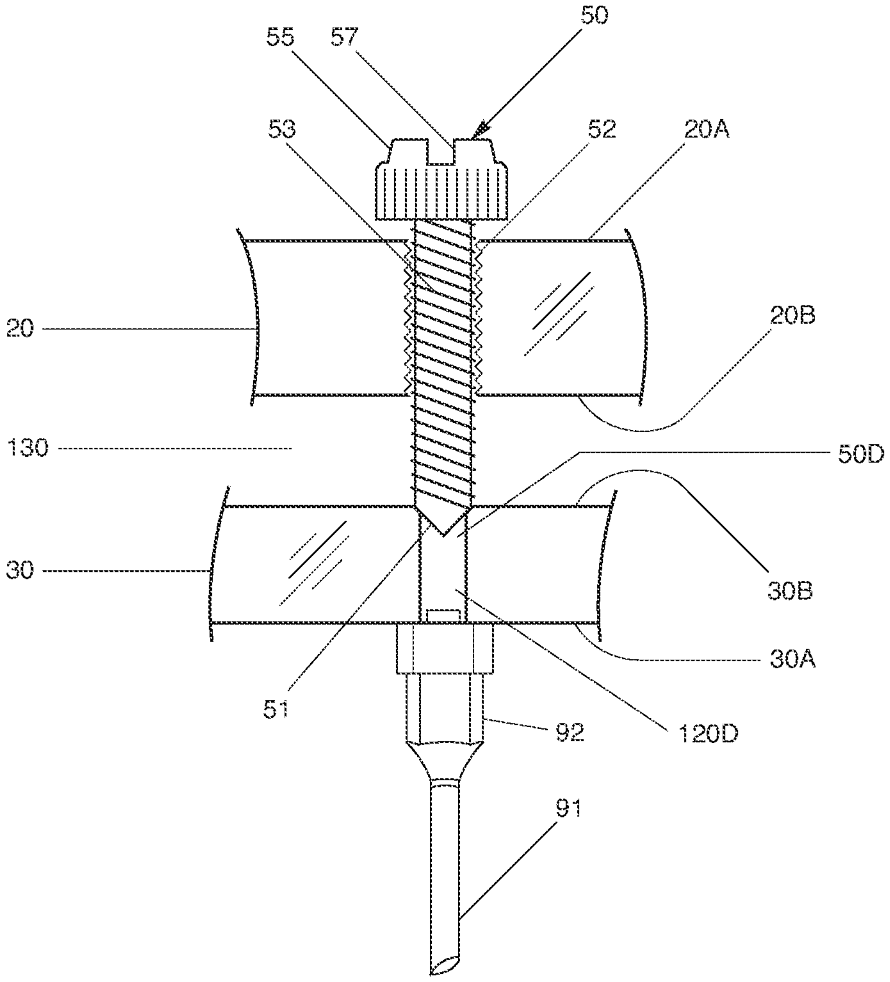
FIG. 6 is a cross-sectional view through the line 4B-4B of FIG. 4A of the evaporator showing one screw in a closing position of its exit port.

Still referring to FIG. 5, the screws 50 have tips 51 that are preferably of a pointed conical shape to closely conform to the corresponding exit ports 120A-C in the bottom plate 30. The top open ends of the exit ports 120A-C are preferably inwardly beveled to mate with the tips 51. The screw 50 can be adjusted so that the screw tip 51 slides into the exit ports 120A-C to the desired gas flow rate. As shown in FIG. 5, the screws 50 can have multiple positions such as open 50A, partially open 50B, and partially closed 50C. Referring to FIG. 6, when the screw 50 is in a closed position 50D, the screw tip 51 fits deeply and snugly into the exit port 120D and precludes gas flow into the nozzles 90.

Referring back to FIG. 3C, a gas travels through the input port 80 and into the gas distribution channel 100 as shown in line A. Next, the gas travels through the gas distribution ports 110A-C of the gas distribution channel 100 to provide an even distribution of gas into the main chamber 130 as shown in line B. The gas exits the main chamber 130 and through the exit ports 120A-F at a gas flow rate independently adjusted an array of screws 50 as shown in line C. Subsequently, the gas flows through exit ports 120A-F and through the nozzles 90 for delivery of the gas into contact with a sample as shown in line D.

The evaporator 10 is designed for concentrating samples of 4 milliters or smaller—a size which is commonly used for storing and transferring samples in analytical and environmental laboratories. For larger sample vials (e.g., 20 or 40 ml vials), the spacing or distances between nozzles 90 can be increased accordingly.

It is noteworthy that the evaporator 10 can be readily adapted for smaller vials. An aluminum sample holder for larger vials (e.g., 40 ml) can be covered with a sheet metal with smaller diameter holes to hold the smaller vials (e.g., 4 ml vial). The evaporator 10 is "downward compatible" as long as the vial diameters are concerned (i.e., those designed for larger diameter vials can be used for smaller diameter vials but not vice versa). Therefore, if a laboratory requires gas introduction into vials of variable sizes, it can acquire the evaporator 10 designed for the largest diameter vials in use.

A specialized sample holder is not required as part of the device, but such a holder provides an easy way to align the sample containers and the nozzles 90. For the evaporator 10, another block of aluminum can hold twenty-four small sample vials in holes machined into the block and arranged to match the dimensions of the nozzles 90. The size of the sample holders and the wells in the holding block are discretionary. Several different holding blocks could be used to facilitate use of different sample holders and sample sizes.

The evaporator 10 can be fitted onto a gear rack (which can be purchased commercially from Boston Gear) for easy adjustment of heights or distances between nozzles 90 and solvent surfaces. This is not required but it does add to the functionality. In this capacity, the evaporator 10 is used more as a gas manifold that is part of a larger concentrator or evaporator device.

The evaporator 10 is used to efficiently evaporate solvent from solutions and suspensions of various materials and/or to introduce gases to multiple reaction media. The evaporator can be used for single or multiple samples or reaction vessels, the latter being processed simultaneously. The evaporator 10 has application in a variety of laboratory settings including, but not limited to, chemical, biological, geological, environmental and physical laboratory analysis.

The evaporator 10 also may contain optional keying posts and corresponding apertures (not shown) to help align the top plate 20 and the bottom plate 30 for proper mating.

Based on the disclosure above, the evaporator 10 is configured to allow equalized gas distribution to the nozzles 90. In addition, the evaporator 10 provides an gas distribution channel 100 with gas distribution ports 110A-C of increasing diameter, in proportion to the a distance D from the input port 80, to provide equalized distribution of gas into the main chamber 130. Also, the evaporator 10 has independent and adjustable screws 50 to control the flow of gas exiting the nozzles 91 via exit ports 120A-F.

It would be appreciated by those skilled in the art that various changes and modifications can be made to the illustrated embodiments without departing from the spirit of the embodiments. All such modifications and changes are intended to be covered by the appended claims.

What is claimed is:

1. An evaporator, comprising:

a main body defining an input port for receipt of an inflow gas, a gas distribution channel in fluid communication with the input port;

the main body further defining a main chamber in fluid communication with the gas distribution channel via a plurality of gas distribution ports, each gas distribution port having a defined aperture to direct the flow of inflow gas in a first direction towards a top portion of the main body, the plurality of gas distribution ports having increasing diameter, in proportion to a distance from the input port, to provide for an even distribution of gas into the main chamber;

at least one exit port defined within the main body and in fluid communication with the main chamber to direct the flow of outflow gas in a second direction opposite of the inflow fluid and through a bottom portion of the main body to allow for equal flow rates in at least one nozzle, the least one nozzle connected adjacent to the main body in respective fluid communication with the at least one exit port, whereby the inflow gas is introduced into the evaporator through the input port and into the gas distribution channel, the inflow gas travels through the input port and into the main chamber to provide an even distribution of gas into the main chamber, thereafter the outflow gas exits the main chamber through the exit port.

2. The evaporator of claim 1, wherein the at least one nozzle is needle connected to the main body with a Leur lock.

3. The evaporator of claim 1, further comprising:

means for controlling gas flow through the at least one exit port.

4. The evaporator of claim 3, wherein the means for controlling gas flow is at least one screw in adjustable threadable engagement with the main body having a tip that respectively resides proximal to the at least one exit port.

5. The evaporator of claim 1, wherein the at least one exit port is a 4×6 array of 24 exit ports.

6. The evaporator of claim 1, wherein the main body includes a first plate and a second plate matable together.

7. The evaporator of claim 6, further comprising:

a gasket residing between the first plate and the second plate.

8. The evaporator of claim 1, wherein the at least one gas distribution port is three gas distribution ports.

9. An evaporator, comprising:

a top plate; and a bottom plate having an input port for receipt of an inflow gas in fluid communication with a gas distribution chamber that terminates in a plurality of gas distribution ports, each gas distribution port having a defined aperture to direct the flow of inflow gas in a first direction towards the top plate;

the top plate and the bottom plate being matable together to provide a main chamber there between;

the plurality of gas distribution ports being in fluid communication with the main chamber, a diameter of the plurality of gas distribution ports increasing in size the further away from the input port;

the bottom plate further including an array of exit ports for distribution of outflow gas in a second direction opposite of the inflow fluid and through the bottom plate to allow for equal flow rates in a plurality of nozzles, the plurality of nozzles connected adjacent to an outer surface of the bottom plate and in respective fluid communication with the exit ports.

10. The evaporator of claim 9, wherein the plurality of nozzles is needles connected to the bottom plate by a Leur lock.

11. The evaporator of claim 9, further comprising:

means for controlling gas flow through the plurality of exit ports.

12. The evaporator of claim 11, wherein the means for controlling gas flow through the plurality of exit ports includes an array of female threaded bores in the top plate with screws, each having a tip, adjustably threadably received therein and in registration with the plurality of exit ports for independent respective control of gas flow through each exit port.

13. The evaporator of claim 12, wherein each tip of the screws complementarily mate with their respective exit port.

14. The evaporator of claim 9, further comprising:

a gasket disposed between the first plate and the second plate thereby preventing leakage of pressurized gas.

15. An evaporator, comprising:

a top plate having an inner and outer surface;

a bottom plate having an inner and outer surface, the inner surface of the bottom plate mated to the inner surface of the top plate to define a main chamber therein used for distribution of gas, the inner surface of the bottom plate defining exit ports for the exit of gas from the main chamber, the exit ports defined within the bottom plate and in fluid communication with the main chamber to direct the flow of outflow gas in a second direction opposite of an inflow fluid to allow for equal flow rates in a plurality of nozzles, the plurality of nozzles connected adjacent to an outer surface of the bottom plate and in respective fluid communication with the exit ports;

an input port for delivery of gas contained within bottom plate and in fluid communication with a gas distribution channel defined within the bottom plate, each gas distribution port having a defined aperture to direct the flow of inflow gas in a first direction towards the top plate, the gas distribution channel having at least one gas distribution port of increasing diameter, in proportion to a distance from the input port, to provide for an even distribution of gas into the main chamber; and whereby the inflow gas is introduced into the evaporator through the input port and into the gas distribution channel, the inflow gas travels through the input port and into the main chamber to provide an even distribution of gas into the main chamber, thereafter the outflow gas exits the main chamber through the port.

* * * * *